Figure 1:
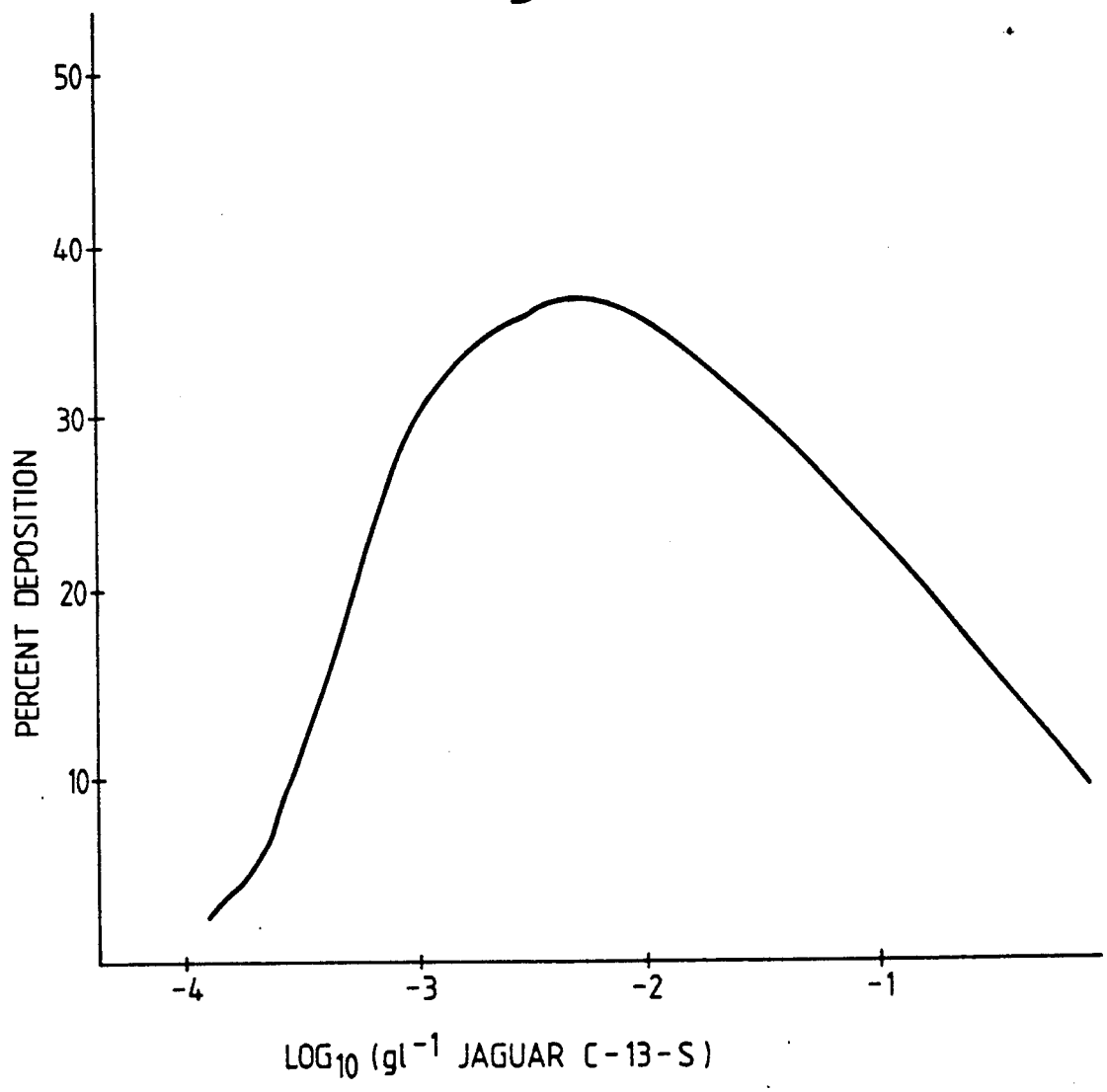

United States Patent [19]

Sime

[11] Patent Number: 5,037,818
[45] Date of Patent: Aug. 6, 1991

[54] WASHING COMPOSITION FOR THE HAIR

[75] Inventor: Stuart J. Sime, South Wirral, United Kingdom

[73] Assignee: Chesebrough-Pond's USA Co., Division of Conopco, Inc., Greenwich, Conn.

[21] Appl. No.: 225,605

[22] Filed: Jul. 26, 1988

Related U.S. Application Data

[63] Continuation of Ser. No. 07/038,435, Apr. 13, 1987, abandoned, which is a continuation of Ser. No. 06/488,513, Apr. 25, 1983, abandoned.

[30] Foreign Application Priority Data

Apr. 30, 1982 [GB] United Kingdom ............... 8212687

[51] Int. Cl.$^5$ .................. A61K 7/06; A61K 9/08; A61K 31/33; A61K 31/395
[52] U.S. Cl. ................... 514/183; 252/106; 252/107; 252/542; 424/70; 424/78; 424/80; 514/881
[58] Field of Search ............ 424/245, 70; 514/183

[56] References Cited

U.S. PATENT DOCUMENTS

| | | | |
|---|---|---|---|
| 3,489,686 | 1/1970 | Parran, Jr. ................ | 424/245 |
| 3,549,546 | 12/1970 | Moore ...................... | 252/542 |
| 3,580,853 | 5/1971 | Parran ...................... | 252/106 |
| 3,761,417 | 9/1973 | Parran ...................... | 252/106 |
| 3,761,418 | 9/1973 | Parran ...................... | 252/106 |
| 3,785,985 | 1/1974 | Grand ....................... | 424/245 |
| 3,862,151 | 1/1975 | Furia et al. ................ | 424/245 |
| 4,470,982 | 9/1984 | Winkler ..................... | 424/245 |

FOREIGN PATENT DOCUMENTS

| | | | |
|---|---|---|---|
| 406375 | 11/1968 | Australia ........................ | 252/106 |
| 18717 | 11/1980 | European Pat. Off. ........... | 252/106 |
| 0034846 | 9/1981 | European Pat. Off. ........... | 424/245 |
| 60611 | 9/1982 | European Pat. Off. ........... | 252/106 |
| 0093541 | 11/1983 | European Pat. Off. ........... | 424/245 |
| 55-116800 | 9/1980 | Japan ............................. | 252/106 |
| 2107586 | 5/1983 | United Kingdom ............... | 424/245 |

OTHER PUBLICATIONS

Norda Briefs, No. 464, Feb. 1975.

Primary Examiner—Dale R. Ore
Attorney, Agent, or Firm—Milton L. Honig

[57] ABSTRACT

The invention concerns a washing composition for washing a surface to deposit thereon substantially water-insoluble particles. The aqueous washing composition of the invention comprises an anionic surfactant, the particulate substance to be deposited and a water-soluble cationic non-cellulosic polymer which enhances the deposition of the particulate substance onto the surface but which cationic polymer does not form in the composition a water-insoluble complex with the anionic surfactant, the cationic charge density of the polymer being from 0.0001 to 0.0017; the concentration of the cationic polymer in the washing composition being from 0.0001% to 0.01% by weight; and the concentration of the surfactant in the washing composition being from 0.01% to 5% by weight.

1 Claim, 3 Drawing Sheets

WASHING COMPOSITION FOR THE HAIR

This is a continuation application of Ser. No. 038,435 filed Apr. 13, 1987, which is a continuation of Ser. No. 488,513, filed Apr. 25, 1983 both now abandoned.

This invention relates to a washing composition for washing a surface to deposit thereon water-insoluble particles, such as particles of a solid antimicrobial substance or the liquid particles of an emulsified oil. In particular the invention relates to an aqueous washing composition comprising an anionic surfactant, the water-insoluble particles and a cationic polymer which serves to enhance the deposition and retention of the particles on the said surface.

Detergent compositions, for example shampoos, comprising an anionic surfactant, water-insoluble particles and a cationic polymer have been described in U.S. Pat. No. 3,580,853 (Parran). In the detergent compositions described in that patent the cationic polymers are water-soluble cationic nitrogen-containing polymers having a molecular weight within the range from 2,000 to 3,000,000 and have a cationic charge density greater than 0.001 in aqueous solution. The "cationic charge density" of a polymer as that term is used in said U.S. Patent, and as used herein, refers to the ratio of the number of positive charges on a monomeric unit of which the polymer is comprised to the molecular weight of said monomeric unit. The cationic charge density multiplied by the polymer molecular weight determines the number of positively charged active sites on a given polymer chain. The Parran patent states that the cationic polymer can be employed in the detergent composition at a concentration within the range from about 0.1% to about 10% by weight, preferably from about 0.25% to about 4.0% by weight.

The Applicant has investigated the mode of action of the enhancement of deposition from liquid detergent compositions of the Examples of the Parran patent containing an anionic surfactant and it appears that the enhancement is dependent upon the precipitation upon dilution of the detergent composition to form an aqueous washing composition of a complex formed between the anionic surfactant and the cationic polymer. The formation of complexes between cationic polymers and anionic surfactants is well-known and is described in Norda Briefs, No. 464, February 1975. This article mentions that such complexes may be solubilised at increased surfactant levels and also refers to the deposition of the water-insoluble complex onto the hair during the shampooing process. The Norda Briefs article refers in particular to those complexes formed using the quaternary nitrogen-substituted cellulose ether derivatives (available commercially under the trade name Polymer JR) which the Parran patent states are particularly efficacious for enhancing the deposition of particulate substances. Applicant's experiments have indicated that in the Parran formulations comprising an anionic surfactant, complexes between the cationic polymer and anionic surfactant precipitate, or separate upon dilution during use and that it is essential for this to occur if an enhancement in the deposition of the particulate substance is to be obtained from the Parran compositions containing an anionic surfactant. While precipitation of the complex and its deposition onto the hair may give a benefit in its own right, for such deposition leads to improved hair condition, more particularly improved ease of combing, such deposition of substantial amounts of cationic polymer is not always desired by the user. It is known for example from European Patent Application No. 80300940 (Publication No. 0 018 717) that deposition of a cationic derivative of a polygalactomannan gum onto the hair during shampooing gives conditioning effects.

Applicant has now found that the presence of certain cationic polymers in aqueous washing compositions comprising an anionic surfactant can enhance the deposition of water-insoluble particles in the absence of the precipitation of a cationic polymer-anionic surfactant complex.

According to the invention there is provided an aqueous washing composition for washing a surface to deposit thereon substantially water-insoluble particles comprising an anionic surfactant, the particulate substance and a water-soluble cationic non-cellulosic polymer for enhancing the deposition, of the particulate substance onto the surface but does not form in the composition a water-insoluble complex with the anionic surfactant, wherein the cationic charge density of the polymer is from 0.0001 to 0.0017; the concentration of the cationic polymer in the washing composition is from 0.0001% to 0.01% by weight; and the concentration of the surfactant in the washing composition is from 0.0% to 5% by weight.

The cationic polymer employed in the washing composition of the invention is a non-cellulosic polymer having a cationic charge density of from 0.0001 to 0.0017 in aqueous solution. In the detergent compositions of the Parran patent the polymers employed have a cationic charge density greater than 0.001 and the lowest specific cationic charge density mentioned is 0.002 for the cellulosic polymer employed in Example XII of that patent. It is to be noted in particular that non-cellulosic polymers having a cationic charge density of 0.0001 to 0.001 are useful in washing composition of this invention but are excluded from the Parran invention. The cationic polymers employed in this invention have a molecular weight within the range from about 2,000 to about 3,000,000 as in the Parran invention.

The non-cellulosic cationic polymers employed in the washing composition of the present invention are present in a concentration of from 0.000% to 0.01% by weight. Below 0.0001% a less satisfactory degree of deposition is obtained and above about 0.01% it may not be possible to avoid the separation of a polymer-surfactant complex. We have found that the amount of particulate substance deposited onto the substrate is dependent upon the concentration of the polymer in the aqueous washing composition.

The preferred cationic polymer for use in the washing composition of the invention is a cationically-substituted galactomannan gum. The gum occurs naturally as guar gum, the principal component of the seed of the guar plant, cyamopsis tetragonalobus. The guar molecule is essentially a straight chain mannan branched at quite regular intervals with single membered galactose units on alternative mannose units. The mannose units are linked to each other by means of beta (1-4) glycosidic linkages. The galactose branching is accomplished through an alpha (1-6) linkage. The cationic derivatives are obtained by reaction between the hydroxyl groups of the polygalactomannan and reactive quaternary ammonium compounds. The degree of substitution of the cationic groups is sufficient to provide a cationic charge density of 0.0001 to 0.0017. The quaternary ammonium compounds which can be used for preparing the cationic agents employed in this invention are those of the general formula

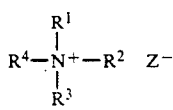

where $R^1$, $R^2$ and $R^3$ are methyl or ethyl groups and $R^4$ is an epoxyalkyl group of the formula

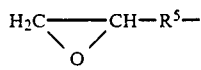

or halohydrin group of the formula

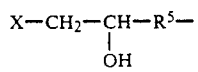

where $R^5$ is a C1-C3 alkylene group and X is chlorine or bromine, Z being an anion such as $Cl^-$, $BR^-$, $I^-$ or $HSO^-_4$.

These reagents would lead to the formation of a galactomannan derivative of the formula

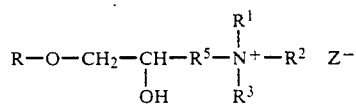

where R represents guar gum.

An example of a suitable quaternary ammonium derivative is hydroxypropyltrimethylammonium guar gum of the formula

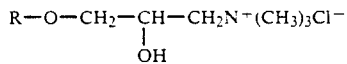

Such a material is available commercially from Celanese-Stein Hall, U.S.A. under thename JAGUAR C-13-S; the word JAGUAR is a trade mark. This material also has the CTFA designation Guar Hydroxypropyltrimonium Chloride. JAGUAR C-13-S has a cationic charge density of 0.0008. Another suitable material is that known as JAGUAR C-17 which is similar to JAGUAR C-13-S but has a higher degree of substitution of cationic groups and has a cationic charge density of 0.0016. A further example of a suitable guar derivative is the hydroxypropylated cationic guar derivative known as JAGUAR C-16 which as well as containing the above cationic quaternary ammonium groups also contains hydroxypropyl ($-CH_2CH(OH)CH_3$) substituent groups. JAGUAR C-16 has a cationic charge density of approximately 0.0008, the degree of substitution of the hydroxypropyl groups being 0.8-1.1.

Other suitable cationic polymers are copolymers of dimethylaminoethylmethacrylate and acrylamide and copolymers of dimethyldiallylammonium chloride and acrylamide in which the ratio of the cationic to neutral monomer units has been selected give a copolymer having a cationic charge density in the required range.

Suitable anionic surfactants for use in the aqueous washing compositions of the invention include alkyl sulphates and alkyl ether sulphates having 8 to 20 carbon atoms in the alkyl group. The ether sulphates may contain an average of from 1 to 10 oxyethylene groups in the molecule. These can be used in the form of their sodium, potassium, ammonium or lower alkanolamine (eg mono-, di- or triethanolamine) salts.

Further suitable anionic surfactants include the sodium or potassium alkyl benzene sulphonates, in which the alkyl group contains from about 9 to about 15 carbon atoms; sodium alkyl glycerol ether sulphonates; sodium coconut oil fatty acid monoglyceride sulphates and sulphonates; sodium salts of sulphuric acid esters of the reaction product of one mole of a higher alcohol (tallow or coconut oil alcohols) and about 3 moles of ethylene oxide; the sulphosuccinates; and the water-soluble salts of condensation products of fatty acids with sarcosine. Conventional soaps may also be used as the anionic surfactant.

Other types of surfactants may be optionally included in the washing composition of the invention. Such other surfactants include the amphoteric and non-ionic surfactants.

Amphoteric surfactants are a well known class of surfactants which includes the alkyl beta-iminodipropionates $RN(C_2H_4COOM)_2$ and the alkyl beta-aminopropionates $RNHCH_4COOM$ where the alkyl group R contains 8 to 18 carbon atoms in both formulae and M is a salt-forming cation such as the sodium ion. Further examples are the long chain imidazole derivatives, for example the di-sodium salt of lauroyl-cycloimidinium-1-ethoxy-ethionic acid-2-ethionic acid, and the substituted betaines such as alkyl dimethyl ammonio acetates where the alkyl group contains 12 to 18 carbon atoms.

Suitable non-ionic surfactants include the polyoxyethylene-polyoxypropylene condensates, which are sold under the trade name "Pluronic"; polyoxyethylene condensates of alkyl phenols; polyoxyethylene condensates of aliphatic alcohols having 8 to 18 carbon atoms, e.g. coconut alcohol/ethylene oxide condensates having from 10 to 30 moles of ethylene oxide per mole of coconut alcohol; polyoxyethylene condensates of sorbitan fatty acids; alkanolamides, such as the monoalkanolamides, dialkanolamides and the ethoxylated alkanolamides, for example coconut monoethanolamide, lauric isopropanolamide and lauric diethanolamide; and amine oxides, for example dodecyldimethylamine oxide.

In the aqueous washing composition of the invention the formation of a water-insoluble complex between the cationic polymer and anionic surfactant is avoided. The maintenance of such a soluble system is favoured by the use of cationic polymers of low cationic charge density, use of low polymer concentrations and use of high surfactant concentrations. Satisfactory combinations of cationic polymer and anionic surfactant are readily found within the ranges set forth above and if, with a given combination of cationic polymer and anionic surfactant within these ranges a complex tends to separate out, variation of the polymer and/or surfactant, for example variation of their relative concentrations, will readily ensure that the combination meets the requirements of the present invention. Generally it is only necessary to avoid the use of the lower surfactant concentrations with the higher concentrations of the more cationic polymers.

The nature of the water-insoluble particles employed in the aqueous washing composition is not critical and a wide variety of materials can be deposited onto various substrates from washing compositions in accordance with the invention. The essential requirement is that the material of the particles should be insoluble or at most only sparingly soluble in water. Materials which it is of practical benefit to deposit on substrates are mentioned in the Parran patent and these can also be employed in the aqueous washing compositions of this invention. These include substances having an average particle diameter of from about 0.2 to about 50 microns and they may be anti-microbial agents, sunscreens, fabric brighteners, and various substances that create a favourable skin feel after washing. One class of particulate substances mentioned in the Parran patent that are of special interest are the salts of pyridinethione (also known as 2-pyridinethiol-1-oxide). The water-insoluble or sparingly water-soluble substance may be employed in the washing composition in an amount of from 0.001% to about 1% by weight.

The washing composition of the invention may take the form of a shampooing composition for the shampooing of hair on the head wherein the water-insoluble particles comprise particles of an anti-microbial agent, particularly a pyridinethione salt, especially zinc pyridinethione or zirconium pyridinethione. However, other shampooing compositions may include particles of a water-insoluble oil having hair conditioning attributes, such oil being emulsified in the composition with the aid of suitable emulsifying agents. The washing composition of the invention may also be one suitable for the washing of fabrics, where the aqueous washing composition comprises particles of a fabric conditioning or treating agent, for example an acrylic latex; or for the washing of hard-surfaces where the aqueous cleaning composition may comprise a germicide, as in, for example, compositions for the cleaning of toilets, or it may comprise a polymer latex designed to leave a polymer film on the cleaned surface, for example to provide a glossy appearance to the surface, or it may comprise a perfume oil. The washing composition of the invention may also find application in the field of oral hygiene where the deposition during use of an oral treatment composition of particles consisting of or comprising an active compound for the care of the oral cavity, including the teeth, may be beneficial.

In the use of the washing composition according to the invention the measure of the enhancement of the deposition of the particulate material is dependent on a number of factors. For a given cationic polymer and a given anionic surfactant, the degree of deposition is dependent on both the concentration of the polymer and on the concentration of the surfactant. There will be a wide range of conditions over which the enhancement is obtained and by simple experimentation those conditions favouring optimum deposition can readily be determined. This variation is illustrated with reference to specific washing compositions given hereinafter. It is believed that the cationic polymer forms, at certain surfactant concentrations above the critical miscelle concentration, a coating on the surface of the water-insoluble particles which does not lie close to the surface of the particles but has loops which extend into the detergent solution and that these loops, because of the positive charges along the polymer chain, provide bridges for attachment to negative sites on the substrate. It should be noted however that the particles will have a net negative charge due to the presence of the anionic detergent. This fact is readily demonstrated by the microelectrophoresis technique. However, the Applicant has discovered that in spite of the net negative charge the cationic polymer can substantially enhance the deposition of the particles onto a negatively charged substrate within the range of conditions described herein. With regard to the above it has to be pointed out that the belief expressed in the Parran patent that the cationic polymer imparts a net positive charge to the involved particles is incorrect in the case of those compositions where the detergent comprises an anionic detergent as in the shampoo compositions described in the Parran patent.

According to another aspect of the invention there is provided a shampoo for washing hair on the head which upon dilution 10 times with water furnishes an aqueous washing composition for washing hair in accordance with the invention and comprising the anionic surfactant in a concentration of 0.8 to 2.5% by weight. The surfactant of the shampoo is preferably an alkyl sulphate or alkyl ether sulphate, present in the shampoo in an amount of 8 to 25 % by weight. As the particulate substance, an antimicrobial substance is preferably used, especially zinc or zirconium pyridinethione in an amount of 0.1 to 3 % by weight.

According to a further aspect of the invention there is provided a detergent composition for cleaning fabrics which upon dilution 250 times with water furnishes an aqueous washing composition for washing fabrics in accordance with the invention, the particulate substance consisting of a fabric conditioning or treating agent.

The invention also relates to a method of washing a surface to deposit thereon substantially water-insoluble particles which comprises contacting the surface with an aqueous washing composition in accordance with the invention.

The following experiments illustrate the invention. Percentages are by weight.

The following description includes accounts of experiments involving the deposition onto various substrates of particles of polystyrene from a polystyrene latex and particles of zinc pyridinethione, respectively, from an aqueous washing composition containing the respective particles. Methods that were used for determining the degree of deposition of these particles will first be described.

In these experiments there was used either a polystyrene latex comprising polystyrene particles of diameter about 0.5 micron and having a solids content of 10%, or a 50% aqueous suspension of zinc pyridinethione particles. Adsorption of particles onto a substrate was monitored by observing their depletion from the treatment medium using a visible spectrophotometer at a wave length of 410 nm. Deposition of these particles onto hair was carried out by the following procedure.

Hair switches of 10 cm length and about 4 grams weight were made from virgin Italian 'Blue String ' hair. The hair was not degreased but was extensively rinsed in running deionized water and combed to remove easily detachable cuticle scales before use. A series of such hair switches which had been stored in deionized water were blotted dry with clean cotton fabric. Each switch was placed in a 10 cm Petri dish with a lid. 5 mls of an aqueous washing composition containing the particles were added from a burette and the switch briefly probed to distribute the liquid and to make sure that it was all taken up into the fibre bundle. The suspension was left in contact with the switch for 2 minutes and then withdrawn slowly with a plastic syringe. The absorbance of the liquid that was withdrawn was then measured. The switches were cleaned by combing vigorously under running deionized water. It was demonstrated that this procedure was adequate to remove the adsorbed particles from the hair. The switches were stored in deionized water before reuse.

The percentage deposition of the particles is given by the expression $(A_o-A) \times 100/A_o$ where $A_o$ is the initial absorbance of the washing composition used to treat the hair and A is the absorbance of the treatment composition after contact with the hair.

In those cases where the aqueous washing composition contained both zinc pyridinethione and a suspending agent so that where there was a co-deposited second phase, the extent of deposition was determined by depletion from the analysis for pyridinethione present in the liquid withdrawn from the treated hair switch.

For the avoidance of doubt, it is to be understood that in the compositions described hereinafter references to zinc pyridinethione as an ingredient thereof refer to the 50% aqueous suspension of zinc pyridinethione, and references to a polystyrene latex as an ingredient refer to the polystyrene latex comprising polystyrene particles having a diameter of about 0.5 micron and having a solids content of 10%.

EXPERIMENT 1

In this experiment the following shampoo compositions were used.

| Ingredient | % Shampoo: A | B | C |
|---|---|---|---|
| Sodium lauryl ether sulphate (2EO) | 11.3 | 11.3 | 11.3 |
| Zinc pyridinethione (50%) | 2.0 | 2.0 | 0.4 |
| Jaguar C-13-S | — | 0.08 | 0.04 |
| ZnSO$_4$.7H$_2$O | 0.1 | 0.1 | 0.1 |
| NaCl | 2.0 | 2.0 | 2.0 |
| Water | ← to 100.0 → | | |

These shampoos were each diluted 10 times with water to form aqueous washing compositions which were used to treat hair switches in the manner described above, except that in order to obtain absorbancies within the range of the spectrophotometer shampoos A and B were diluted a further 10 times after deposition of the zinc pyridinethione and before measurement. The results are given below in Table 1.

TABLE 1

| Shampoo | % Deposition | Amount of deposit relative to deposit from Shampoo A |
|---|---|---|
| A | 11 ± 4 | 1 |
| B | 79 ± 6 | 7.2 |
| C | 54 ± 7 | 0.98 |

The data show that deposition of the zinc pyridinethione was considerably enhanced by the inclusion of the cationic polymer Jaguar C-13-S. In particular the results show that Shampoo C containing the cationic polymer but containing only one-fifth of the amount of the zinc pyridinethione present in Shampoo A deposited substantially the same amount of the particulate zinc compound onto the treated hair switches as did Shampoo A.

Neither Shampoo B or C on dilution gave rise to a precipitate of a polymer-surfactant complex. The systems are clear (in the absence of the zinc pyridinethione) and remain so upon dilution demonstrating that no complex separates.

EXPERIMENT 2

Experiments were conducted with three other trimethyl ammonium hydroxypropyl guars having cationic charge densities different from that of Jacquar C-13-S, namely 0.0004, 0.0016 and 0.0018. The shampoos tested had the following compositions:

| Ingredient | % Shampoo: D | E | F | G |
|---|---|---|---|---|
| Sodium lauryl sulphate | 14.4 | 4.2 | 14.4 | 14.4 |
| Trimethylammonium hydroxypropyl guar[1] | — | 0.01 | — | — |
| Trimethylammonium hydroxypropyl guar[2] | — | — | 0.01 | — |
| Trimethylammonium hydroxypropyl guar[3] | — | — | — | 0.01 |
| Polystyrene latex[4] | ← qs → | | | |
| Water | ← to 100 → | | | |

[1] of cationic charge density 0.0004
[2] of cationic charge density 0.0016 (Jaguar C-17)
[3] of cationic charge density 0.0018
[4] sufficient latex was present to give a convenient absorbance reading The shampoos were diluted 10 times with water to form the aqueous washing compositions used to treat the hair switches in the manner described above.

The results are given in Table 2.

TABLE 2

| Shampoo | % Deposition |
|---|---|
| D | 0 ± 6 |
| E | 27 ± 5 |
| F | 31 ± 6 |
| G | 0 ± 3 |

The results show that the guar derivatives having cationic charge densities of 0.0004 and 0.0016 were effective in enhancing deposition, whereas that of charge density 0.0018 was not effective in enhancing deposition.

None of the shampoos E, F and G when diluted with water to give the washing compositions used to treat the hair switches formed an insoluble complex of the polymer and the surfactant.

EXPERIMENT 3

In this experiment cationic polymers other than guar derivatives were employed. These were the following:

Polymer A - a quaternised copolymer of dimethylaminoethyl methacrylate and acrylamide having a cationic charge density of 0.0002.

Polymer B - a dimethyldiallylammonium chloride/acrylamide copolymer having a cationic charge density of 0.0015.

Polymer C - poly(dimethyldiallylammonium chloride) having a cationic charge density of 0.006.

The following shampoos were used in this experiment.

| Ingredient | % Shampoo: H | I | J | K |
|---|---|---|---|---|
| Sodium lauryl sulphate | 14.4 | 14.4 | 14.4 | 14.4 |
| Polymer A | — | 0.01 | — | — |
| Polymer B | — | — | 0.01 | — |

-continued

| Ingredient | % Shampoo: | | | |
|---|---|---|---|---|
| | H | I | J | K |
| Polymer C | — | — | — | 0.004 |
| Polystyrene latex[1] | ← qs → | | | |
| Water | ← to 100.0 → | | | |

[1] sufficient latex was present to give a convenient absorbance reading.

The shampoos were diluted 10 times with water to form the aqueous washing compositions used to treat the hair switches.

The results are given in Table 3.

TABLE 3

| Shampoo | % Deposition |
|---|---|
| H | 0 ± 6 |
| I | 29 ± 5 |
| J | 27 ± 5 |
| K | −3 ± 4 |

The results again show that the cationic polymers of cationic charge density above 0.0017 are not effective in enhancing deposition.

None of the shampoos I, J and K gave rise to the separation of a polymer-surfactant complex when diluted with water to form the aqueous washing compositions used to treat the hair switches.

EXPERIMENT 4

The following shampoos were used in this experiment.

| Ingredient | % Shampoo: | |
|---|---|---|
| | L | M |
| Sodium lauryl ether sulphate (3EO) | 10.0 | — |
| Lauryl triethoxy monosulphosuccinate | — | 5.0 |
| Jaguar C-13-S | 0.01 | 0.01 |
| Polystyrene latex[1] | ← qs → | |
| Water | ← 100.0 → | |

[1] sufficient latex was present to give a convenient absorbance reading

The shampoos were diluted 10 times with water to form the aqueous washing compositions used to treat the hair switches in the manner described above.

The deposition from each shampoo was compared with that from the corresponding shampoo obtained by omitting the cationic polymer. These shampoos are referred to below as shampoos L' and M', respectively. The results are given in Table 4.

TABLE 4

| Shampoo | % Deposition |
|---|---|
| L(L') | 60 ± 3 (10 ± 4) |
| M(M') | 44 ± 3 (8 ± 2) |

The results show that in each case the presence of the cationic polymer resulted in an improvement in deposition.

Neither of shampoos L and M gave rise to the separation of a cationic polymer-surfactant complex when diluted with water to form the aqueous washing composition used to treat the hair switches.

EXPERIMENT 5

The following shampoos were formulated.

| Ingredient | % Shampoo: | |
|---|---|---|
| | N | O |
| Triethanolamine lauryl sulphate | 16.6 | 16.6 |
| Lauryl isopropanolamide | 3.5 | 3.5 |
| Ethylene glycol monostearate | 3.0 | 3.0 |
| Jaguar C-13-S | — | 0.04 |
| Zinc pyridinethione (50%) | 0.4 | 0.4 |
| ZnSO$_4$.7H$_2$O | 0.1 | 0.1 |
| NaCl | 2.0 | 2.0 |
| Water | to 100.0 | to 100.0 |

The shampoos were diluted 10 times with water to form the aqueous washing compositions used to treat the hair switches in the manner described above.

The deposition of the zinc pyridinethione was determined by analysis for pyridinethione of the liquid withdrawn after treatment of the hair switches since in this experiment the cationic polymer also enhanced deposition of the ethylene glycol monostearate.

The results are given in Table 5.

TABLE 5

| Shampoo | % Deposition of Zinc Pyridinethione |
|---|---|
| N | 11 ± 5 |
| O | 50 ± 3 |

Shampoo O did not give rise to the separation of a polymer-surfactant complex when it was diluted with water to give the aqueous washing composition used to treat the hair switches.

EXPERIMENT 6

The effect of variation in the concentration of cationic polymer in the aqueous washing composition is shown by the curve of FIG. 1 of the drawings.

The vertical axis represents the percentage deposition and the horizontal axis is the logarithm to the base 10 of the concentration in grams per liter of the cationic polymer which was Jaguar C-13-S.

The curve relates to the deposition of the polystyrene latex (as used in the experiments described previously) from a surfactant solution of constant concentration of $5 \times 10^{-2}$ moles, the surfactant being sodium lauryl sulphate.

In this experiment no separation of a polymer-surfactant complex from the washing compositions occurred.

EXPERIMENT 7

Figure 2:
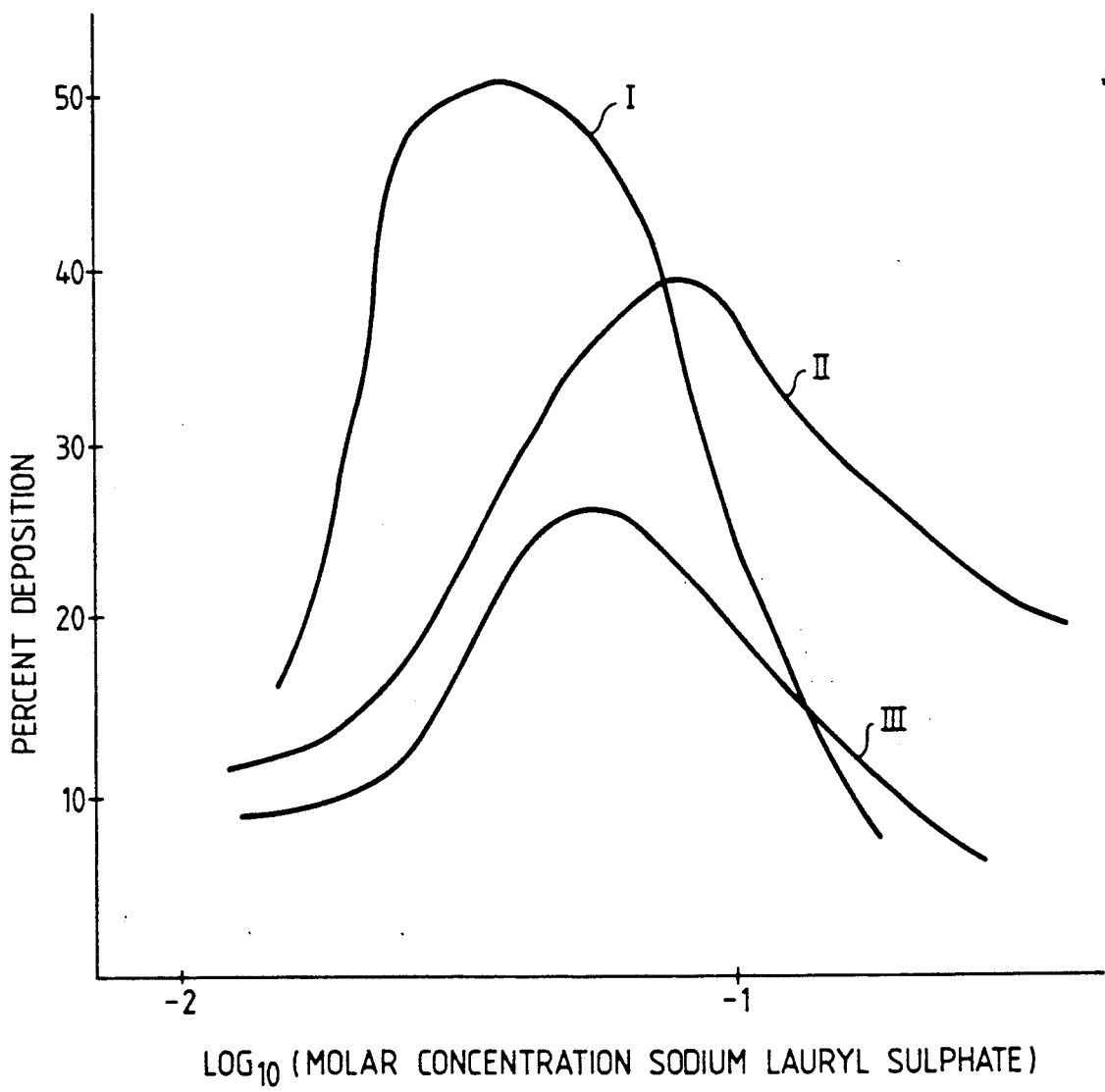

The effect of varying the surfactant concentration in the washing composition at constant concentration of the cationic polymer ($10^{-2}$ gl$^{-1}$) is shown in FIG. 2 of the accompanying drawings.

The vertical axis is the same as that of FIG. 1 and the horizontal axis is the logarithm to the base 10 of the molar concentration of the surfactant which was sodium lauryl sulphate. The curves were obtained from experiments in which the particles being deposited onto hair were those of a polystyrene latex as described above.

The curves were obtained using different cationic polymers as follows:
curve I—Jaguar C-13-S
II—Polymer A of Experiment 3
III—Polymer B of Experiment 3.

In this experiment no separation of a polymer-surfactant complex from the washing compositions occurred.

In the absence of a cationic polymer the deposition of the polystyrene particles was about 1%.

EXPERIMENTS 8

This experiment concerns the effect of varying the concentration of the surfactant triethanolamine lauryl sulphate (TLS) on the deposition of particles of zinc pyridinethione (0.125 gl$^{-1}$) in the presence of the cationic resin Jaguar C-13-S at a constant concentration of $10^{-2}$gl$^{-1}$. The results are given in Table 6.

TABLE 6

| TLS concentration (%) | % Deposition |
| --- | --- |
| 0.1 | 29 ± 4 |
| 0.3 | 39 ± 6 |
| 0.5 | 41 ± 5 |
| 1.0 | 45 ± 5 |
| 2.0 | 47 ± 5 |
| 3.0 | 44 ± 5 |
| 5.0 | 43 ± 7 |

There is no separation of a polymer-surfactant complex under any of the conditions employed in this experiment.

EXPERIMENT 9

Figure 3:
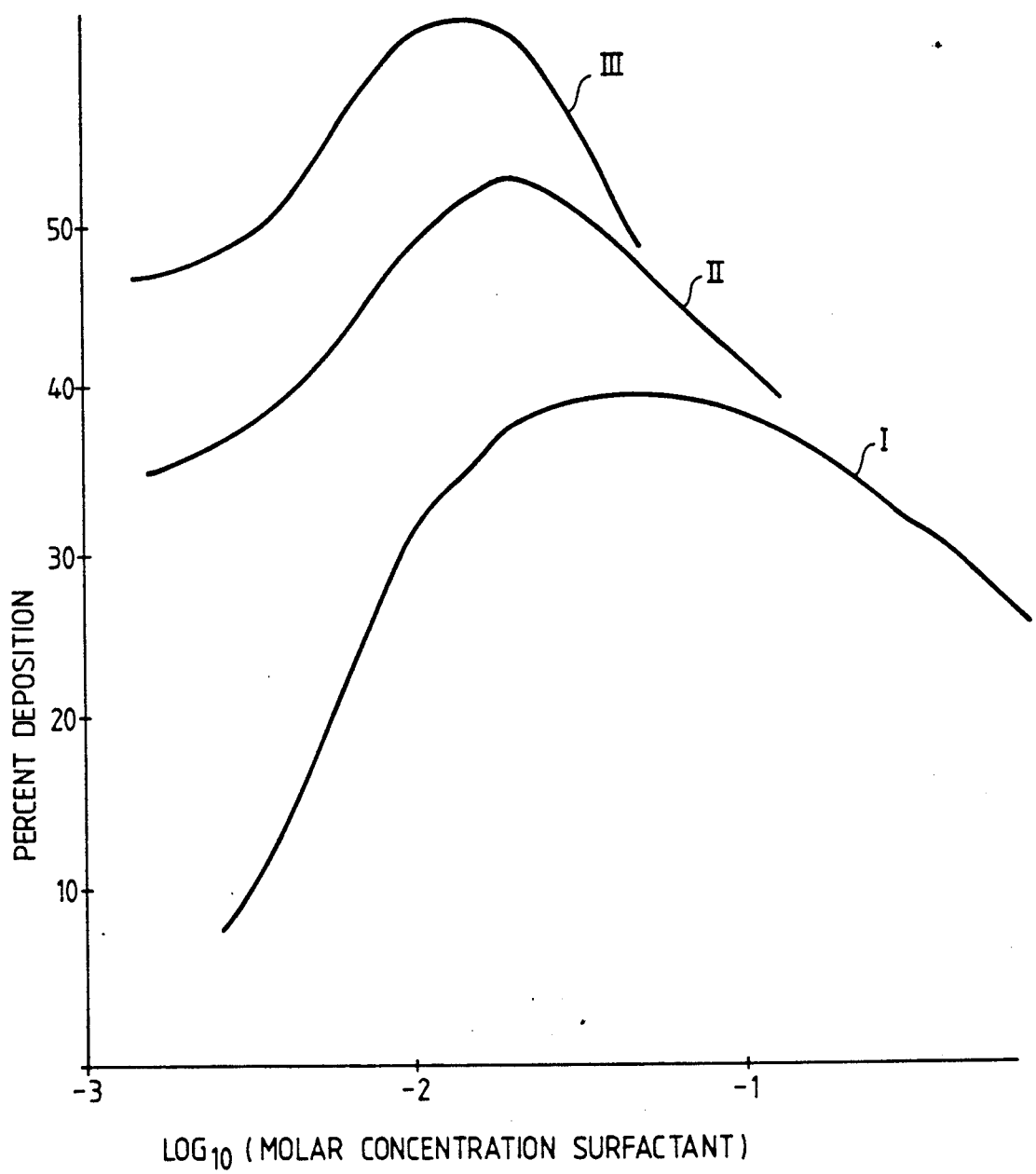

This experiment shows that the concentration of the surfactant for maximum deposition depends on the type of detergent used. This is shown by the curves of FIG. 3 of the accompanying drawings which show the effect on deposition of particles (the polystyrene latex referred to above being used in these tests) of variation in surfactant concentration at a constant concentration of $10^{-2}$ gl$^{-1}$ of the cationic polymer Jaguar C-13-S. The curves relate to the use of different surfactants as follows:

| Curve | Surfactant |
| --- | --- |
| I | sodium lauryl ether sulphate (2EO) |
| II | sodium lauryl ether sulphate (3EO) |
| III | Lauryl triethoxy monosulphosuccinate |

In this experiment no separation of a polymer-surfactant complex from the washing compositions occurred.

EXPERIMENT 10

In this experiment shampoos containing cationic cellulosic polymers were employed but these cationic polymers did not lead to enhancement of the deposition of the particulate substances. The shampoos employed in these tests had the following compositions:

| Ingredient | % Shampoo: P | Q | R |
| --- | --- | --- | --- |
| Sodium lauryl sulphate | 14.4 | — | 14.4 |
| Sodium lauryl ether sulphate (2EO) | — | 12.0 | — |
| Polymer JR 400[1] | 0.01 | — | — |
| Polymer JR 125[2] | — | 0.04 | — |
| Calquat H 100[3] | — | — | 0.01 |
| Polystyrene latex[4] | qs | — | qs |
| Zinc pyridinethione (50%) | — | 0.25 | — |
| Water | ← to 100.0 → | | |

[1]a cationic polymer of the type described in U.S. Pat. No. 3,472,840, viscosity of 2% solution at 25° C. being 300-500 cp, and having a cationic charge density of 0.0013.
[2]similar to Polymer JR 400 but of lower molecular weight, the viscosity of a 2% solution at 25° C. of being 75-175 cp, the cationic charge density being 0.0013.
[3]a water-soluble quaternary cellulose derivative containing 1% quaternary nitrogen and having a cationic charge density of 0.0007.
[4]sufficient latex was present to give a convenient absorbance reading.

As previously, these shampoos were diluted 10 times with water to form the washing compositions used to treat the hair switches. There was no separation of a polymer-surfactant complex from the washing compositions.

EXPERIMENT 11

In this experiment a cationic polymer of relatively high charge density was employed. This was the polymer known commercially as Nafloc 600 (available from the Nalco Chemical Company). It is copolymer of tetraethylene pentamine and epichlorohydrin. A shampoo was made up having the following composition:

| Ingredients | % Shampoo: S |
| --- | --- |
| Sodium lauryl sulphate | 10 |
| Nafloc 600 | 2 |
| Zinc pyridinethione | 4 |
| Water | to 100 |

The deposition of zinc pyridinethione was determined by analysis for pyridinethion.

It was determined that on dilution of the shampoo, no enhancement of deposition from the washing composition thus produced occurred until the degree of dilution was sufficient to give rise to the separation of a complex of the cationic polymer and the anionic surfactant.

EXPERIMENT 12

This experiment concerns the deposition of a hair conditioning oil onto hair from a hair washing composition.

An emulsion of 0.1% of a hair conditioning oil was made in a 3% solution of sodium lauryl ether sulphate (2EO) also containing 0.02% each of polyoxyethylene (20) sorbitan monooleate and sorbitan monooleate as emulsifying agents. Two hair washing compositions were prepared. One (Composition T) was prepared by mixing 20 ml of the above emulsion with 20 ml of a $4\times10^{-2}$gl$^{-1}$ Jaguar C-13-S solution and the other (Composition T') was prepared from 20 ml of the emulsion and 20 ml of deionized water. Deposition experiments were carried out as described carried out as described previously. The deposition from each hair washing composition was measured, five times. The percentage deposition of the oil onto the hair was again given by the expression (Ao-A)×100/Ao where Ao and A have the above meanings. The results are given in Table 7.

TABLE 7

| Treatment Solution | % Deposition |
| --- | --- |
| T | 37 ± 5 |

TABLE 7-continued

| Treatment Solution | % Deposition |
|---|---|
| T' | 20 ± 3 |

The results show that the presence of the cationic polymer, Jaguar C-13-S, enhanced the deposition of the hair conditioning oil during the treatment of the hair switches.

No separation of any complex occurred in composition T.

EXPERIMENT 13

This experiment concerns the deposition of a fabric treatment latex from a fabric washing composition.

Two fabric washing compositions were made up in deionized water. One composition (Composition U') contained 0.03% of sodium dodecylbenzene sulphonate, 0.01% of a polyoxyethylene (7EO) ether of isomeric $C_{11}-C_{15}$ linear secondary alcohols, 0.08% sodium tripolyphosphate and sufficient of a self-reactive vinyl-acrylic copolymer latex (available commercially for fabric treatment under the name VINACRYL 4322 from Vinyl Products) to give a convenient initial absorbance reading from the spectrophotometer. The second composition (Composition U) contained the same ingredients as that of Composition U' but additionally comprised $4 \times 10^{-3}$ gl$^{-1}$ of the cationic polymer Jaguar C-13-S. The procedure described above for carrying out the deposition experiment was followed but was slightly modified by replacing the hair switch by 1.5g of a pre-hydrated cotton fabric. The results are given in Table 8 where the percentage deposition of the vinyl-acrylate copolymer onto the cotton fabric is again given by the expression $(Ao-A) \times 100/Ao$ where Ao and A have the above meanings.

TABLE 8

| Washing Composition | % Deposition |
|---|---|
| U | +10 ± 2 |
| U' | −4 ± 2 |

It will be noted that in the absence of the cationic polymer a slightly higher absorbance was observed after the treatment composition containing the latex had been in contact with the cotton fabric. This suggests that although the cotton fabric had been pre-hydrated some uptake of water by the fabric still occurred to a small extent.

The results show that a greater deposition of the latex occurred from the washing composition containing the cationic polymer.

No separation of any polymer-surfactant complex occurred in composition U.

EXPERIMENT 14

This experiment concerns the deposition of a gloss-enhancing polymer latex from a hard-surface cleaner composition.

The hard-surface cleaner formulation employed had the following composition.

| Ingredient | % |
|---|---|
| Sodium dodecyl benzene sulphonate | 10.5 |
| Nonionic surfactant[1] | 2.0 |
| Sodium tripolyphosphate | 5.0 |
| Urea | 6.0 |
| Water | to 100.0 |

[1] a polyoxyethylene (8EO) ether of isomeric $C_9-C_{11}$ linear secondary alcohols.

This formulation was diluted 50 times in one case with a $4 \times 10^{-3}$ gl$^{-1}$ solution of the cationic polymer Jaguar C-13-S to give washing composition V and in another case with deionized water to give washing composition V'. In each solution there was included sufficient of a styrene-acrylic copolymer latex which forms glossy films (available commercially under the name VINACRYL 7170 from Vinyl Products) to give a convenient reading on the spectrophotometer. Corresponding washing compositions W and W' were formulated by diluting the above formulation 500 times instead of 50 times.

As a model of a hard polar surface substrate, and to obtain a sufficiently high surface area of contact between the surface and the suspension, glass wool (about 0.8g dry weight) was used in place of the hair switch in the deposition experiment described previously. The percentage deposition of the styrene-acrylic polymer onto the glass wool, as given by the expression $(Ao-A) \times 100/Ao$, is given below in Table 9 for the various treatment products referred to above.

TABLE 9

| Washing Composition | % Deposition |
|---|---|
| V | 21 ± 3 |
| V' | 7 ± 3 |
| W | 20 ± 3 |
| W' | 1 ± 2 |

The results show that the presence of the cationic polymer in the compositions V and W significantly enhanced the deposition of the styrene-acrylic latex onto the substrate as contrasted with the degree of deposition obtained using the corresponding suspensions V' and W', respectively, not containing the cationic polymer.

No separation of any polymer-surfactant complex occurred in either of compositions V and W.

I claim:

1. An aqueous shampooing composition for washing hair to deposit thereon substantially water-insoluble anti-microbial particles, comprising from 0.1% to 5% by weight of an anionic surfactant selected from the group consisting of alkyl sulfate and alkyl ether sulfate, from 0.001% to 1% by weight of anti-microbial particles of zinc pyridinethione and from 0.0001% to 0.01% by weight of a water-soluble cationic non-cellulosic galactomannan gum polymer for enhancing the deposition of the particles onto the hair but which cationic polymer does not form in the composition a water-insoluble complex with the anionic surfactant, wherein the cationic charge density of the polymer is 00.0008.

* * * * *